United States Patent [19]

Rumanowski

[11] 4,288,610
[45] Sep. 8, 1981

[54] PURIFICATION OF PYRETHROID INTERMEDIATE COMPOUNDS BY SELECTIVE PARTIAL SAPONIFICATION

[75] Inventor: Edmund J. Rumanowski, Dover, N.J.

[73] Assignee: Stauffer Chemical Company, Westport, Conn.

[21] Appl. No.: 123,879

[22] Filed: Feb. 25, 1980

[51] Int. Cl.³ .................. C07C 67/60; C07C 69/743; C07C 69/747
[52] U.S. Cl. .................................................. 560/124
[58] Field of Search ......................................... 560/124

[56] References Cited

U.S. PATENT DOCUMENTS

| | | | |
|---|---|---|---|
| 3,538,143 | 11/1970 | Matsui | 560/124 |
| 3,652,652 | 3/1972 | Julia | 560/124 |
| 3,931,280 | 1/1976 | Nagase | 560/124 |
| 3,943,167 | 2/1976 | Suzukamo | 560/124 |

Primary Examiner—Natalie Trousof
Assistant Examiner—Michael Shippen
Attorney, Agent, or Firm—William C. Gerstenzang

[57] ABSTRACT

Saponifiable impurities are removed from pyrethroid intermediates represented by the structure

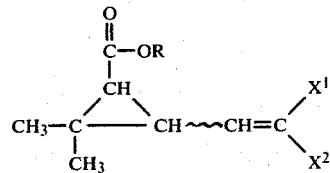

wherein R represents an alkyl radical having from 1 to about 30 carbon atoms and wherein $X^1$ and $X^2$ each represent a halogen by selectively saponifying said impurities by reaction with an aqueous base.

7 Claims, No Drawings

PURIFICATION OF PYRETHROID INTERMEDIATE COMPOUNDS BY SELECTIVE PARTIAL SAPONIFICATION

BACKGROUND OF THE INVENTION

The present invention relates to a method for the purification of pyrethroid intermediates. More particularly, the present invention relates to a method by which certain byproducts formed during the preparation of pyrethroid intermediates may be removed therefrom.

Pyrethroid intermediates are very important industrial raw materials in that they provide ready access to highly active insecticides. Thus, for example, it is known to react a pyrethroid intermediate, such as permethrin acid ester (PAE) with a cyanohydrin ester, such as metaphenoxybenzaldehyde cyanohydrin acetate to form a potent insecticide, such as NRDC-149 as follows:

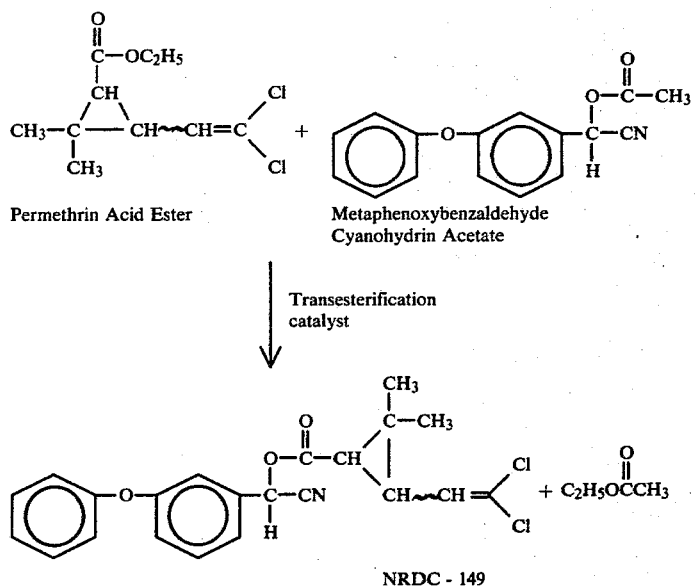

NRDC - 149

It is generally desirable that the pyrethroid intermediate, whether used to prepare insecticides or for other purposes, be relatively free of impurities. Unfortunately, however, the pyrethroid intermediates are often contaminated by the presence of other compounds which are formed as byproducts in the production of the intermediate.

Thus, for example, in Pesticide Science (1974) 5, 791-799 it is shown that the reaction between ethyl diazoacetate and 1,1-dichloro-4-methylpenta-1,3-diene in the presence of copper sulfate to produce ethyl 2,2-dimethyl-3-(2,2-dichlorovinyl)-cyclopropanecarboxylate, results in a product which is contaminated with up to 20% of ethyl fumarate and maleate.

These contaminants are very difficult to remove because they co-distill with the product compound.

In an article by Andre T. Hubert in *Synthesis*, 1976, p. 600 it is reported that column chromatography or Gas-Liquid chromatography can be employed to separate the desired product from the maleate and fumarate contaminants to produce a pure product.

The use of such techniques, however, is not practical on an industrial scale.

A need therefore exists for an industrially-practical method for purifying the pyrethroid intermediates.

SUMMARY OF THE INVENTION

It has now been found that the pyrethroid intermediates can be separated from saponifiable impurities contained therein by partially saponifying the mixture of the intermediate compound and saponifiable impurities under such conditions as to selectively saponify the saponifiable impurities.

More specifically, it has been found that when the contaminated pyrethroid intermediate is brought into contact with a limited amount of a base under controlled conditions of pH and temperature, essentially all of the saponifiable impurities can be reacted with the base with little or no effect on the pyrethroid intermediate itself.

DETAILED DESCRIPTION OF THE INVENTION

In accordance with the present invention there is provided a process for removing saponifiable impurities from compositions comprising the saponifiable impurities and a pyrethroid intermediate compound represented by the structural formula:

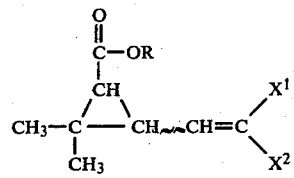

wherein R is an alkyl radical having from 1 to about 30 carbon atoms and wherein $X^1$ and $X^2$ are each independently selected from the group consisting of fluorine, bromine, chlorine and alkyl having from 1 to about 10 carbon atoms, which comprises reacting said composition with an aqueous base in an amount and under conditions sufficient to selectively saponify said saponifiable impurities so that they become soluble in said aqueous base, and separating said pyrethroid intermediate compound from said aqueous base.

The pyrethroid intermediate compounds for which the process of the present invention is most useful are those which are prepared by the reaction of a diazoacetate, such as ethyl diazoacetate and a diene, such as 1,1-dichloro-4-methyl-1,3-pentadiene. The compounds prepared by this reaction often contain as much as 20% by weight of saponifiable impurities, which are principally comprised of the maleate and fumarate byproducts of the reaction. The invention is, however, applicable to pyrethroid intermediate compounds in general, which are contaminated with saponifiable impurities.

For ease in handling, the pyrethroid intermediate may be dissolved in an inert solvent, such as ethanol; but it is not necessary to do so.

In a particularly preferred embodiment of the present invention the pyrethroid intermediate compound is the compound of structure I wherein R is ethyl, and $X^1$ and $X^2$ are both chlorine.

The impurities which are present and which are removed in accordance with the present invention are most frequently principally comprised of the maleate and fumarate esters of R.

The base which is used in the practice of the present invention can be any one of several known to those skilled in the art. These include, but are not limited to, dilute aqueous solutions of sodium hydroxide, potassium hydroxide, sodium carbonate, potassium carbonate, sodium bicarbonate and potassium bicarbonate, although sodium hydroxide is preferred.

As used herein, the term "dilute" means an aqueous solution of the base having a base concentration ranging from about 0.1% by weight to about 10% by weight, although concentrations ranging from about 0.3% to about 3% are preferred.

The amount of base used in the practice of the present invention is preferably slightly in excess of the stoichiometric amount required to saponify the saponifiable impurities. This is because a small amount of the pyrethroid intermediate compound is usually also saponified, thereby consuming some of the base.

Although the approximate amount of base required can be calculated when the nature and amount of saponifiable impurities is known, it is preferred to determine the actual amount required through pH measurements. That is to say, it is preferred to continue adding base solution to the mixture until a predetermined pH endpoint is reached.

The pH at which the process of the present invention is conducted ranges from about 8 to about $11\frac{1}{2}$. At lower pH's the reaction rate can be slower than desirable and the degree of completion of the reaction can be less than desirable. At higher pH's the impurities will be saponified, as desired, but excessive amounts of the pyrethroid intermediate compound can also be saponified.

Preferably, no more than about 10% by weight of the pyrethroid intermediate compound itself will be saponified.

A particularly-preferred pH range is from about $9\frac{1}{2}$ to about $10\frac{1}{2}$. This pH range can be measured using ordinary pH (litmus) paper, which is the preferred method to use in the practice of the present invention.

The base solution should be added to the mixture in such a way as to maintain the pH of the resulting reaction mass within the pH limits given. Such addition can be made, for example, in a dropwise manner, a continuous manner or in several portions over a measured period of time. Preferably, the base solution is added continuously or semi-continuously, with the rate of addition adjusted to maintain the pH within the desired limits. Completion of the desired reaction will be indicated by a pH end-point within the desired range. More specifically, reaction completion will be achieved when the pH can be held within the desired range for a period of about 5 minutes with no further base addition.

The temperature at which the reaction is conducted preferably ranges from about 20° C. to about 45° C. At temperatures above this range the amount of pyrethroid intermediate compound which is saponified along with the impurities can become significant, which would represent a loss of desired product. At temperatures below the range, the reaction rate can be less than desirable.

A particularly preferred temperature range is from about 25° C. to about 35° C.

Although the reaction which takes place is somewhat exothermic in nature, the exotherm is relatively unnoticable since it is relatively minor.

Once the reaction has been completed, as indicated by a stable pH, the reaction mass should be permitted to settle to form an aqueous phase and a nonaqueous phase.

The nonaqueous phase will comprise the purified pyrethroid intermediate compound, while the aqueous phase will comprise an aqueous solution of the base and salts of the saponified impurities.

The nonaqueous phase can be separated from the aqueous phase by decantation.

In order that the present invention be more fully understood, the following examples are given by way of illustration. No specific details or enumerations contained therein should be construed as a limitation on the present invention except insofar as they appear in the appended claims.

EXAMPLE 1

To a 250 ml. three-neck flask equipped with stirring, heating and cooling means was added 20 grams of Permethrin Acid Ester (PAE), having a purity of 95% by weight with 50 ml. of ethanol and a few drops of phenolphtalein. The flask contents were maintained at 45°–50° C. as a 3% wt. aqueous solution of sodium hydroxide was slowly added until a permanent red endpoint was reached. It was observed that the flask contents became milky towards the end of the sodium hydroxide addition.

The flask contents were permitted to settle into an aqueous phase and an organic phase, which were then separated.

50 ml. of water was added to the aqueous phase, which caused additional organic material to settle out. This was recovered and combined with the organic material recovered initially.

The aqueous phase was then mixed with 50 ml. of methylene chloride to extract organic material therefrom, after which the methylene chloride was recovered and discarded.

The aqueous phase was acidified, which caused a trace amount of organic material to come out of solution.

The organic phase was washed with 100 ml. of water, then vacuum stripped (10 mm Hg) at 70° C. The final product weighed 16.5 grams (82.5% of original charge).

The original permethrin acid ester and the purified permethrin acid ester were each analyzed by gas-liquid chromatography with the following results.

|  | Original | Product |
|---|---|---|
| Permethrin Acid Ester (cis) | 41.1% | 42.1 |
| Permethrin Acid Ester (trans) | 54.0 | 56.2 |
| Fumarate | 0.42 | 0.1 |
| Maleate | 0.06 | 0.01 |
| Unknown | 2.6 | 0.8 |
| Total Weight | 20 gm | 16.5 gm |
| Total % permethrin acid ester | 95.1% | 98.3% |
| Total wt. permethrin acid ester | 19 gm | 16.2 gm |
| % permethrin acid ester recovered | — | 85.3% |

This example shows that the process of the present invention was effective in improving the purity of permethrin acid ester from 95% to 98.3%.

EXAMPLE 2

To a 250 ml. three-neck flask equipped with stirring, heating and cooling means was added 25 grams of impure permethrin acid ester, 50 ml. of ethanol and 3 drops of phenolphtalein. The temperature of the flask contents was adjusted to 25° C. A 3% aqueous sodium hydroxide solution was added portionwise over a period of 1½ hours until the flask contents developed a permanent red color.

The reaction mixture was then diluted with 75 ml. water and permitted to settle into an aqueous phase and an organic phase. The two phases were separated.

Methylene chloride was used to extract additional organic material from the aqueous phase.

The aqueous phase was then treated with acid—no haze or organic precipitate was formed.

The combined organic material (i.e., that recovered by phase separation and that extracted from the aqueous phase) was then dried over magnesium sulfate and stripped. The final product weighed 24 grams.

Analysis of the permethrin acid ester (PAE) both before and after the experiment was made by gas-liquid chromatography, with the following results.

|  | Before | After |
|---|---|---|
| Cis PAE | 41.1 | 41.5 |
| Trans PAE | 54.0 | 56.3 |
| Fumarate | 0.42 | 0.09 |
| Maleate | 0.06 | 0.03 |
| Unknown | 2.6 | 0.26 |
| Total wt. | 25 gm | 24 gm |
| Total % PAE | 95.1 | 97.8 |
| Total wt. PAE | 23.8 gm | 23.5 gm |
| % PAE recovered | — | 98.7% |

This example shows that when the permethrin acid ester was purified by the process of the present invention at 25° C., 98.7% of the original material was recovered.

EXAMPLE 3

In substantially the same manner as in Example 2, 25 grams of impure permethrin acid ester (PAE) was purified, with the following results.

|  | Before | After |
|---|---|---|
| Cis PAE | 40.91 | 42.7 |
| Trans PAE | 52.26 | 55.2 |
| Fumarate | 0.14 | 0.12 |
| Maleate | 0.16 | 0.07 |
| Unknown | 5.20 | 0.6 |
| Total wt. | 25 gm | 23 gm |
| Total % PAE | 93.17 | 97.9 |
| Total wt. PAE | 23.29 | 22.52 |
| % PAE recovered | — | 96.7 |

EXAMPLE 4

The procedure of Example 3 was repeated except that a less pure sample of permethrin acid ester (PAE) was used, the sodium hydroxide was added to an endpoint of pH 12 as measured by pH meter (phenolphthalein endpoint is estimated to be about pH 9) and a 6% sodium hydroxide solution was used instead of a 3% solution. The results were as follows.

|  | Before | After |
|---|---|---|
| Cis PAE | 46.3 | 57.2 |
| Trans PAE | 30.3 | 37.0 |
| Fumarate | 5.1 | 0.08 |
| Maleate | 6.9 | 3.1 |
| Unknown | 6.3 | 1.0 |
| Total wt. | 25 gm | 19 gm |
| Total % PAE | 76.6 | 94.2 |
| Total wt. PAE | 19.15 | 17.89 |
| % PAE recovered | — | 93.5% |

This example shows that when the saponification was conducted at a pH of 12, the product recovery was reduced to 93.5%.

EXAMPLE 5

To a 250 ml. three-neck flask equipped with stirring, heating and cooling means was added 25 grams of impure permethrin acid ester (PAE) together with 50 ml. of ethanol. Aqueous sodium hydroxide in the amount of 25 ml. and at a concentration of 4% wt. was then added and the resulting mixture was held at 30°-35° C., with stirring, for 30 minutes.

Water, in the amount of 100 ml. and ethylene dichloride, in the amount of 25 ml., was then added, with stirring. The flask contents were permitted to settle into an aqueous phase and an organic phase, which were separated from each other. The pH of the aqueous phase was measured with litmus paper and found to be about pH 9.

Ethylene dichloride was used to extract additional organic material from the aqueous phase, which material was then added to the organic phase.

The combined organic phase was washed with 25 ml. water, after which it was stripped to 5 mm Hg. at 65° C. to yield 22.3 grams of purified product.

The results are tabulated below.

|  | Before | After |
|---|---|---|
| Cis PAE | 48.8 | 52.2 |
| Trans PAE | 39.2 | 41.8 |
| Fumarates | 0.6 | 0.01 |
| Maleates | 1.2 | — |
| Unknown | 3.45 | 0.01 |
| Total wt. | 25 gm | 22.3 gm |
| Total % PAE | 88 | 94 |
| Total wt. PAE | 22 | 21.0 |

| | Before | After |
|---|---|---|
| % PAE recovered | — | 95.3% |

EXAMPLE 6

A sodium hydroxide solution was prepared by adding 6.3 g of 50% sodium hydroxide to 50 ml water.

Impure permethrin acid ester, in the amount of 26.8 grams, was added together with 30 ml. ethanol to a 250 ml. three neck flask equipped with stirring, heating and cooling means. The temperature of the flask contents was maintained at 30°–35° C. while the sodium hydroxide solution was added over a period of one hour. After the sodium hydroxide has been added, the pH of the flask contents was determined to be between 9 and 10 using litmus paper.

The flask contents were transferred to a separatory funnel and diluted with 100 ml. water and 25 ml. ethylene dichloride. The contents were permitted to settle into an aqueous phase and an organic phase, after which the organic phase was removed.

Additional organic material was extracted from the aqueous phase by washing with 25 ml. ethylene dichloride, which organic material was added to the organic phase.

The organic phase was stripped to 5 mm Hg at 70° C. to yield 14.5 grams of final product.

The results, as determined by gas-liquid chromatography, were as follows:

| | Before | After |
|---|---|---|
| Cis PAE | 36.5 | 56.4 |
| Trans PAE | 22.1 | 34.7 |
| Fumarates | 13.4 | 0.02 |
| Maleates | 19.2 | 0.08 |
| Unknown | 0.7 | 0.02 |
| Total wt. | 26.8 | 14.5 |
| Total % PAE | 58.6 | 91.1 |
| Total wt. PAE | 15.7 | 13.2 |
| % PAE recovered | — | 84.1% |

I claim:

1. A process for removing saponifiable impurities from a composition comprising said saponifiable impurities and a pyrethroid intermediate compound represented by the structural formula:

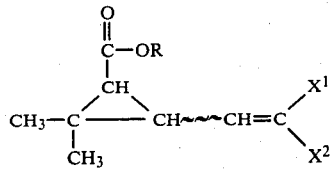

wherein R is an alkyl radical having from 1 to about 30 carbon atoms and wherein $X^1$ and $X^2$ are each independently selected from the group consisting of fluorine, bromine, chlorine and alkyl having from 1 to about 10 carbon atoms and wherein said saponifiable impurities comprise the maleate and fumarate esters of R, which comprises reacting said composition with a dilute aqueous base in an amount and under conditions sufficient to selectively saponify said saponifiable impurities so that they become soluble in said aqueous base, and separating said pyrethroid intermediate compound from said aqueous base.

2. The process of claim 1 wherein said base is an aqueous solution of sodium hydroxide, potassium hydroxide, sodium carbonate, potassium carbonate, sodium bicarbonate or potassium bicarbonate.

3. The process of claim 2 wherein said base is an aqueous solution of sodium hydroxide having a concentration ranging from about 0.1% to about 10% by weight.

4. The process of claim 1 wherein the amount of said base is the amount required to obtain a pH endpoint of from about 8 to about 11 ½.

5. The process of claim 4 wherein said reaction is conducted at a temperature ranging from about 20° C. to about 40° C. and at a pH ranging from about 8 to about 11 ½.

6. The process of claim 1 wherein said pyrethroid intermediate compound is the product of the reaction between a diazoacetate and a pentadiene.

7. The process of claim 1 wherein said pyrethroid intermediate compound is permethrin acid ester.

* * * * *